(12) United States Patent
Kim et al.

(10) Patent No.: US 9,019,495 B2
(45) Date of Patent: Apr. 28, 2015

(54) APPARATUS FOR PERFORMING SPECTROSCOPY HAVING A POROUS MEMBRANE

(75) Inventors: Ansoon Kim, Mountain View, CA (US); Zhiyong Li, Foster City, CA (US); Steven J. Barcelo, Mountain View, CA (US); Zhang-Lin Zhou, Palo Alto, CA (US); Gary Gibson, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 196 days.

(21) Appl. No.: 13/563,362

(22) Filed: Jul. 31, 2012

(65) Prior Publication Data

US 2014/0036263 A1 Feb. 6, 2014

(51) Int. Cl.
*G01J 3/44* (2006.01)
*G01N 21/65* (2006.01)
*G01N 21/77* (2006.01)

(52) U.S. Cl.
CPC ......... *G01N 21/658* (2013.01); *Y10T 29/49826* (2015.01); *G01N 2021/775* (2013.01)

(58) Field of Classification Search
USPC .................... 356/301, 72–73; 422/69; 29/428
See application file for complete search history.

(56) References Cited

U.S. PATENT DOCUMENTS

| 2010/0087723 A1 | 4/2010 | Van Duyne et al. |
| 2010/0182607 A1* | 7/2010 | Chau et al. ................... 356/445 |
| 2011/0171137 A1* | 7/2011 | Patolsky et al. ................ 424/9.3 |

* cited by examiner

*Primary Examiner* — Abdullahi Nur
(74) *Attorney, Agent, or Firm* — Mannava & Kang, P.C.

(57) ABSTRACT

According to an example, an apparatus for performing spectroscopy includes a structure having an opening. The apparatus also includes a plurality of surface-enhanced Raman spectroscopy (SERS) elements positioned within the structure and a porous membrane covering the opening and the plurality of SERS elements. The porous membrane is to allow a predetermined analyte to reach the SERS elements while substantially preventing other analytes from reaching the SERS elements.

14 Claims, 5 Drawing Sheets

APPARATUS FOR PERFORMING SPECTROSCOPY HAVING A POROUS MEMBRANE

BACKGROUND

In surface-enhanced Raman scattering (SERS), vibrationally excitable levels of an analyte are probed. The energy of a photon shifts by an amount equal to that of the vibrational level (Raman scattering) excited by the photon. A Raman spectrum, which consists of a wavelength distribution of bands corresponding to molecular vibrations specific to the analyte being probed, may be detected to identify the analyte. In SERS, the analyte molecules are in close proximity, for instance, less than tens of nanometers, to metal nano-particles that may be or may not be coated with a dielectric, such as silicon dioxide, silicon nitride, and a polymer, that, once excited by light, set up plasmon modes, which create near fields around the metal nano-particles. These fields can couple to analyte molecules in the near field regions. As a result, concentration of the incident light occurs at close vicinity to the nano-particles, enhancing the Raman scattering from the analyte molecules.

SERS have recently been performed to probe fluids in vivo through implantation of the metal nano-particles subcutaneously. However, because fluids typically contain multiple types of species, some of the species that are not desired to be detected may bind onto the metal nano-particles or otherwise block the active sensing area. Permanent binding of the species of interest is also undesirable, as it limits the potential for continuous sensing. As a result conventional SERS devices are often unable to provide accurate measurements of desired species.

BRIEF DESCRIPTION OF THE DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared, near infrared, and ultra-violet portions of the electromagnetic spectrum.

Disclosed herein are an apparatus for performing spectroscopy and a method for fabricating the apparatus. The apparatus disclosed herein comprises a structure having an opening. In addition, a plurality of surface-enhanced Raman spectroscopy (SERS) elements are positioned within the structure. A porous membrane is provided over the opening and the SERS elements, such that the porous membrane operates to filter fluid introduced into the structure. Thus, for instance, the porous membrane substantially prevents relatively large molecules, and in certain instances variously shaped and/or various type of species of molecules, from entering into the structure.

In one regard, the filtering function of the porous membrane may significantly increase targeted analysis of analyte molecules by preventing relatively large and untargeted molecules from substantially blocking the near fields generated by the SERS elements. The targeted analysis of the analyte molecules may further be enhanced through functionalization of the surfaces of the SERS elements to preferentially bind with a predetermined species as discussed herein below.

According to an example, the apparatus disclosed herein may be intended for implantation into a specimen, such as a human, a dog, a plant, a non-living item, etc., to enable in situ spectroscopy operations to be performed using the apparatus. The apparatus may be implanted directly or the apparatus may be placed into a housing, such as a surgically implantable stent, prior to being implanted. In addition, the apparatus disclosed herein may be fabricated from biocompatible, biodegradable resistant, and antithrombolytic materials. Alternatively, however, the apparatus disclosed herein may be implemented in conditions where the apparatus is not implanted into a specimen.

Through implementation of the apparatus disclosed herein, in vivo or in vitro molecular imaging may be performed in a continuous manner over a relatively long period of time. In addition, as the apparatus is fabricated with biocompatible materials, the apparatus may not be toxic or may have reduced toxicity as compared with alternative techniques. Moreover, by preventing relatively large molecules from being introduced onto the SERS elements, the apparatus may be used over a relatively long period of time because the relatively large molecules are substantially prevented from blocking the near fields generated by the SERS elements.

Figure 1A:
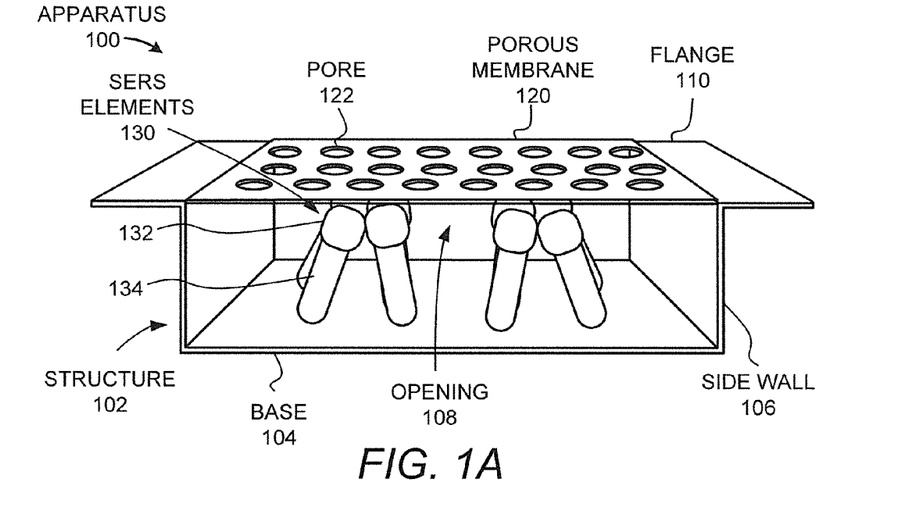
FIGS. 1A and 1B, respectively show cross-sectional perspective views of an apparatus for performing spectroscopy, according to an example of the present disclosure.
Figure 1B:
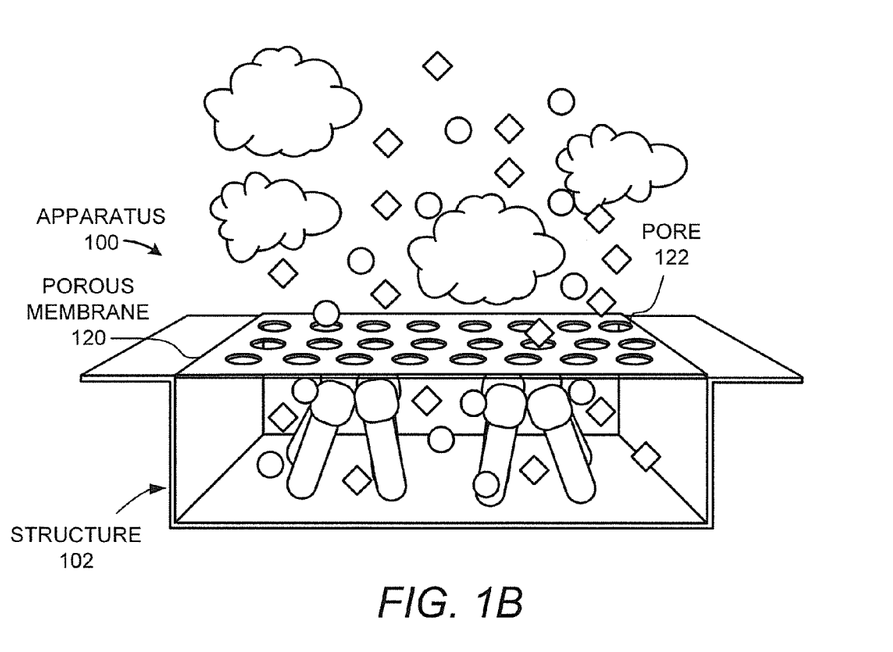

With reference first to FIGS. 1A and 1B, there are respectively shown cross-sectional perspective views of an apparatus 100 for performing spectroscopy, according to an example. It should be understood that the apparatus 100 depicted in FIGS. 1A and 1B may include additional components and that some of the components described herein may be removed and/or modified without departing from a scope of the apparatus 100. It should also be understood that the components depicted in FIGS. 1A and 1B are not drawn to scale and thus, the components may have different relative sizes with respect to each other than as shown therein.

The apparatus 100 may be implemented to perform spectroscopy, which is also equivalently referred herein as surface-enhanced Raman spectroscopy (SERS), to detect a molecule in an analyte sample with a relatively high level of sensitivity. As a particular example, the apparatus 100 is to be implemented to perform spectroscopy following implantation of the apparatus 100 into a specimen, such as a human, chimpanzee, dog, cat, plant, non-living item, etc., or in any gaseous or liquid environment where accurate analysis of target species is desired. The apparatus 100 may thus be implemented to analyze molecules in a fluid in a specimen, such as blood, saliva, interstitial fluid, sweat, urine, subcutaneous tissue, muscular tissue, analyte carried by a gas, air, etc. The apparatus 100 may alternatively be implemented in spectroscopy applications that do not involve implantation of the apparatus 100, for instance the detection of melamine in milk contained in a vial.

As shown, the apparatus 100 includes a structure 102, a porous membrane 120, and SERS elements 130. The structure 102 depicted in FIGS. 1A and 1B includes a base 104 and side walls 106. The structure 102 may also include side walls 106 in the front and the back of the structure, such that the structure 102 comprises one opening 108 surrounded by the side walls 106, and thus comprises a well structure. The structure 102 may also include an interior wall (not shown) to form multiple sub-structures and openings 108. The structure 102 may further include multiple openings 108, such that fluid may flow into the structure 102 through one of the openings 108 and out of the structure 102 through the other opening 108, for instance, as shown in FIG. 2D. The structure 102 is also depicted as including flanges 110, which may be used to support the structure 102 inside of a housing, such as a stent, which is described in greater detail below. The flanges 110 may be optional as the apparatus 100 may be implemented without the flanges 110, for instance, when the apparatus 100 is implemented outside of a housing.

The structure 102 may be composed of any suitable material that is sufficiently rigid to substantially maintain a predetermined shape. According to an example, the structure 102 is composed of a material that is suitable for implantation into a specimen. Examples of suitable materials comprise polymers, metals, surgical grade plastics, etc. According to an example, and as discussed in greater detail below, the apparatus 100 comprises a surgically implantable stent. In addition, the structure 102 may be formed through any of a variety of different fabrication techniques, including nanoimprinting, molding, stamping, etc. According to a particular example, at least one of the base 104 and a side wall 106 is fabricated to be optically reflective, for instance, through coating of the interior structure 102 surface(s) with at least one of a metal, such as gold, silver, etc., a protective coating of dielectric material, Bragg layers, etc. According to another particular example, at least one of the walls of the structure 102 is optically transparent, for instance, to enable excitation light and/or Raman scattered light to be emitted through the wall.

According to an example, at least one of the length and the width of the structure 102 is on the order of about 1 micron and the height of the structure 102 is less than about 1 micron. In other examples, the smallest dimension of the structure 102 is on the order of about 1 micron to 100 microns. By way of particular example, the structure 102 has a width of about 1 micron and a length of about 10 microns.

The porous membrane 120 is positioned to span and cover the opening 108, such that a fluid is required to pass through the porous membrane 120 in order to enter into the structure 102. In this regard, the porous membrane 120 is to block various materials from entering into the structure 102 and therefore filter the fluid entering into the structure 102. As shown in FIG. 1B, a fluid comprises a plurality of different types of molecules, in which, only certain ones of the molecules are allowed to pass through the pores 122. In the example depicted in FIG. 1B, only molecules having a sufficiently small size to fit through the pores 122 are able to enter into the structure 102. As discussed in greater detail below, however, the pores 122 may also have particular shapes to enable selective entry of molecules having particular shapes. In addition, or alternatively, the porous membrane 120 may be functionalized with receptors of molecules that are not expected to pass through the pores 122. In this example, the porous membrane 120 may be functionalized with receptors of various types of molecules so that multiple species in the fluid may be selectively and efficiently blocked. The porous membrane 120 may be functionalized in the manners discussed below with respect to FIG. 1C.

The porous membrane 120 may also be formed to enable light, including excitation light and Raman scattered light to substantially pass therethrough. In this example, the porous membrane 120 may be formed with sufficiently configured pores 122, of sufficiently thin size and/or an optically transparent material to enable the light to pass therethrough. By way of particular example, the porous membrane 120 has a thickness that is between about 10 nm to about 100 nm. Although the porous membrane 120 has been depicted as having a relatively thin configuration, the porous membrane 120 may alternatively have a thicker, sponge-like, configuration.

The porous membrane 120 may be held in position over the opening 108 through use of, for instance, medical grade glue, or other biocompatible adhesives. In addition, the porous membrane 120 may be composed of any suitable material that enables the porous membrane 120 to perform the functions in the apparatus 100 discussed herein. Examples of suitable materials for the porous membrane 120 include cellulose acetate, urethane based polymer (for example, polyurethane, polyether urethane, or polycarbonate urethane), ethylene glycol based polymer, heparin-functionalized polymer, a combination of these materials, etc.

Moreover, the porous membrane 120 may be fabricated to include pores 122, in which the pores 122 are sized to allow molecules that are smaller than a predetermined size to pass through the pores 122, while preventing larger molecules from passing therethrough. By way of example, the pores 122 may be fabricated into the porous membrane 120 through implementation of a molecular imprinting technique. In this technique, for instance, molecules that are to be allowed to pass through the porous membrane 120 are mixed with a polymer material and the mixture is formed into a relatively thin sheet and resist cured, e.g., UV cured. The molecule is then dissolved from the relatively thin sheet of mixed material, thereby leaving pores that are specially shaped to the molecules that are to be allowed to pass through the porous membrane 120. The thin sheet of material may then be positioned on a supporting porous sub-layer (not shown) and the combined layers may be positioned over the opening 108 and attached to the structure 102.

According to another example, the porous membrane 120 comprises a lipid bilayer, which is a thin polar membrane made of two layers of lipid molecules. The lipid bilayer comprises relatively flat sheets of lipid molecules that form a continuous barrier around cells. The lipid bilayer includes proteins that serve as transporting vehicles through the lipid bilayer membrane. In this regard, the proteins may selectively transport molecules, for instance, molecules having sufficiently small sizes to pass through the lipid bilayer membrane, through the lipid bilayer membrane, which therefore enables the lipid bilayer membrane to operate as a filter. The lipid bilayer may be collected from naturally occurring cells and/or fabricated synthetically from lipid molecules. In any regard, the lipid bilayer may be positioned, for instance, by coating the lipid bilayer, on a supporting porous sub-layer (not shown) and the combined layers may be positioned over the opening 108 and attached to the structure 102.

According to a further example, the porous membrane 120 may be functionalized to include host molecules, such as crown ethers, cyclodextrins, etc., that are to bond to corresponding guest molecules. Because the molecules corresponding to the host molecules bond to the host molecules, the corresponding guest molecules are substantially prevented from entering into the structure 102 through the porous membrane 120.

The SERS elements 130, which comprise Raman-enhancing elements arranged in various ordered or random configurations, are depicted as being positioned above the base 104 of the structure 102. The SERS elements 130 may one or both of enhance Raman scattering and facilitate analyte adsorption. The SERS elements 130 generally enhance sensing operations, such as, surface enhanced Raman spectroscopy (SERS), enhanced luminescence, etc., to be performed on molecules positioned on or near the SERS elements 130.

The SERS elements 130 comprise Raman-enhancing elements 132, such as nanoparticles or nanostructures, which may comprise plasmonic materials such as but not limited to, gold (Au), silver (Ag), and copper (Cu). The Raman-enhancing elements 132 may have nanoscale surface roughness, which is generally characterized by nanoscale surface features on the surface of the layer(s) and may be produced spontaneously during deposition of the plasmon-supporting material layer(s). By definition herein, a plasmon-supporting material is a material that facilitates Raman scattering and the production or emission of the Raman signal from an analyte on or near the material during Raman spectroscopy. In addition, the Raman-enhancing elements 132 of the SERS elements 130, e.g., plasmonic nanostructures, may be deposited onto a substrate formed, for instance, of a polymer material, a metallic material, a semiconductor material, etc., through, for instance, physical vapor deposition (PVD), chemical vapor deposition (CVD), sputtering, etc., of metallic material, or self-assembly of pre-synthesized nano-particles. Alternatively, the Raman-enhancing elements 132 may be deposited and/or formed directly on a surface of the base 104.

According to a particular example, and as shown in FIG. 1A, the SERS elements 130 also comprise nano-fingers 134 upon which the Raman-enhancing elements 132 are formed. Various manners in which the nano-fingers 134 and the Raman-enhancing elements 132 may be formed into the configurations depicted in FIG. 1A are described in detail below.

Figure 1C:
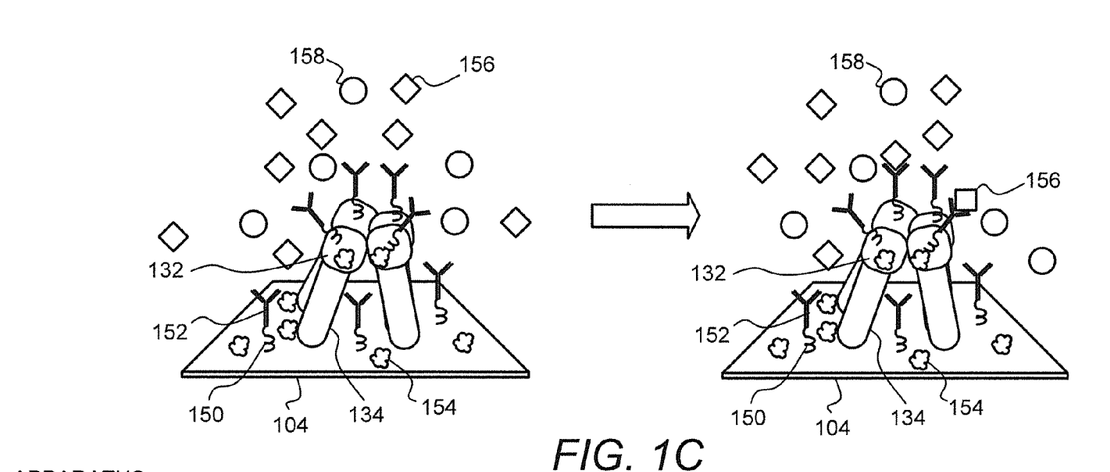
FIG. 1C shows two diagrams of a portion of the apparatus depicted in FIGS. 1A and 1B prior to and following binding by a particular type or species of molecule onto a receptor, according to an example of the present disclosure.

Turning now to FIG. 1C, there are shown two diagrams of a portion of the apparatus 100 prior to and following binding by a particular type of molecule onto a receptor, according to an example. In FIG. 1C, a portion of the base 104, a plurality of Raman-enhancing elements 132, and a plurality of nano-fingers 134 are shown. In addition, the surfaces of the Raman-enhancing elements 132 are depicted as being functionalized to bind with particular molecules. Particularly, the surfaces of the Raman-enhancing elements 132, as well as the surface of the base 104, have been functionalized with molecule linkages 150, receptors 152, and blocking agents 154 that prevent nonspecific binding. The receptors 152 are to specifically bind to desired species of molecules and the blocking agents 154 are to prevent nonspecific binding from occurring by samples. In this regard, the selected molecules 156 may bind with the receptors 152, while other molecules 158 may not bind with the receptors 152. According to a particular example, the molecule linkages 150 and the receptors 152 comprise biocompatible molecule linkages 150 and biocompatible receptors 152.

The functionalization depicted in FIG. 1C may be performed through any suitable technique. For instance, the functionalization may be performed through any suitable chemical process, in which the molecule linkages 150, the receptors 152, and the blocking agents 154 are supplied onto the SERS elements 130 in one or more stages. By way of example, the receptors 152 may be modified with the molecule linkages 150 to become bonded to the Raman-enhancing elements 132 as well as to become biocompatible. As another example, the molecule linkages 150 may first be bonded to the Raman-enhancing elements 132 followed by chemically reacting with the receptors 152 to form the receptor-functionalized SERS elements 130. In any regard, the functionalization of the SERS elements 130 generally increases the likelihood that enhanced Raman signals from target molecules 156 will be generated.

According to a particular example, the functionalization is performed to cause relatively weak bonds to be formed between the receptors 152 and the target molecules 156. In this example, the target molecules 156 may relatively easily bind with and detach from the receptors 152. In addition, under an equilibrium state, for instance, when a predetermined concentration of target molecules 156 is present in a fluid, a generally predictable number of target molecules 156 may bind with the receptors 152 at any given time, resulting in a generally particular Raman signal emission level from the target molecules 156. As the concentration of the target molecules 156 decreases, the number of target molecules 156 that bind with the receptors 152 will likely decrease as the target molecules 156 may be detached from the receptors 152, thereby decreasing the Raman signal emission level from the equilibrium state. Additionally, as the concentration of the target molecules 156 increases, the number of target molecules 156 that bind with the receptors 152 will likely increase because of the increased likelihood of the target molecules 156 binding with the receptors 152. In this regard, the concentration of the target molecules 156 in a fluid sample may be estimated based upon a detected Raman signal level. In addition, the apparatus 100 may be implemented to estimate the concentration of the target molecules 156 at a particular time. Moreover, the apparatus 100 may be used multiple times to estimate the concentration of the target molecules 156 in the sample fluid at different points in time, which may increase the useful lifetime of the apparatus 100.

Figure 2A:
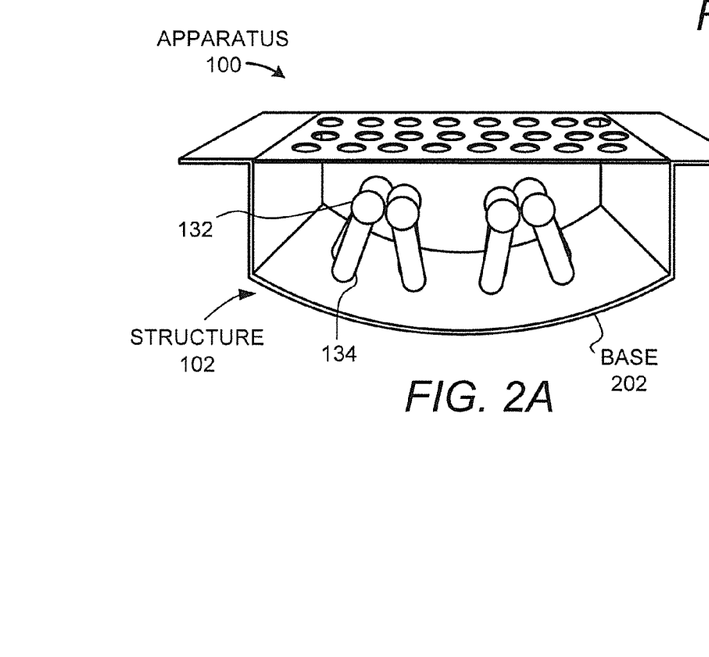
FIGS. 2A and 2B, respectively show perspective views of the apparatus depicted in FIGS. 1A and 1B, according to two other examples of the present disclosure.
Figure 2B:
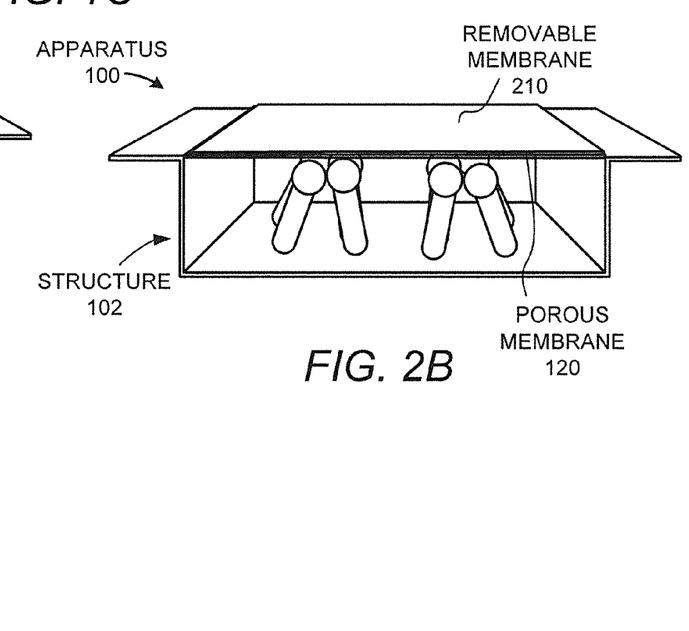

With reference now to FIGS. 2A and 2B, there are respectively shown perspective views of the apparatus 100, according to two other examples. Particularly, in FIG. 2A, the structure 102 is depicted as including a base 202 having a curved configuration. In one example, the top surface of the curved base 202 may be reflective, for instance, to reflect Raman scattered light emitted from molecules in the near field generated by the Raman-active material nano-particles 132 into a direction outside of the structure 102. For instance, the Raman scattered light may be reflected from a reflective surface of the curved base 202 into a collimated or nearly collimated beam. By way of example, the reflective surface of the curved base 202 may focus the Raman scattered light onto an optical device, such as an aperture, a lens, etc., to direct the Raman scattered light toward a detector.

In FIG. 2B, the apparatus 100 is depicted as including a removable membrane 210 covering the porous membrane 120. Particularly, the removable membrane comprises a barrier that is impervious to a fluid, and more particularly, the molecules that are to flow through the porous membrane 120. In this regard, the removable membrane 210 blocks fluid from flowing through the porous membrane 120. As such, in order to introduce fluid to be analyzed into the structure 102, the removable membrane 210 is to be removed, thereby exposing the porous membrane 120. According to an example, the removable membrane 210 is composed of a material, such as a degradable polymer, that is to decompose, for instance, when illuminated by a relatively intense beam of light. In another example, the removable membrane 210 may be composed of a material that is biodegradable, for instance, following a predictable time after being implanted inside a specimen. In one regard, the removable membrane 210 enables control over introduction of the sample fluid into the structure 102, for instance, following implantation of the apparatus 100.

Figure 2C:
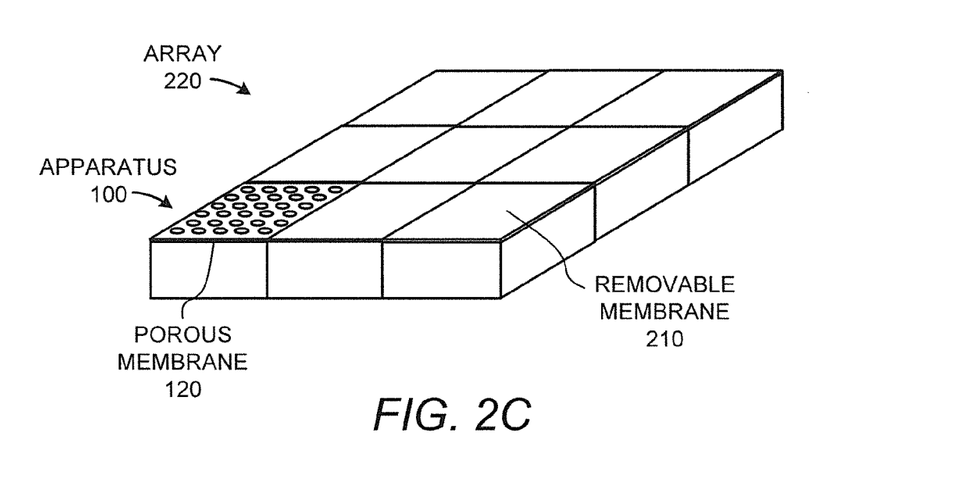
FIG. 2C shows an isometric view of an array of the apparatuses depicted in FIG. 2B, according to an example of the present disclosure.
Figure 2D:
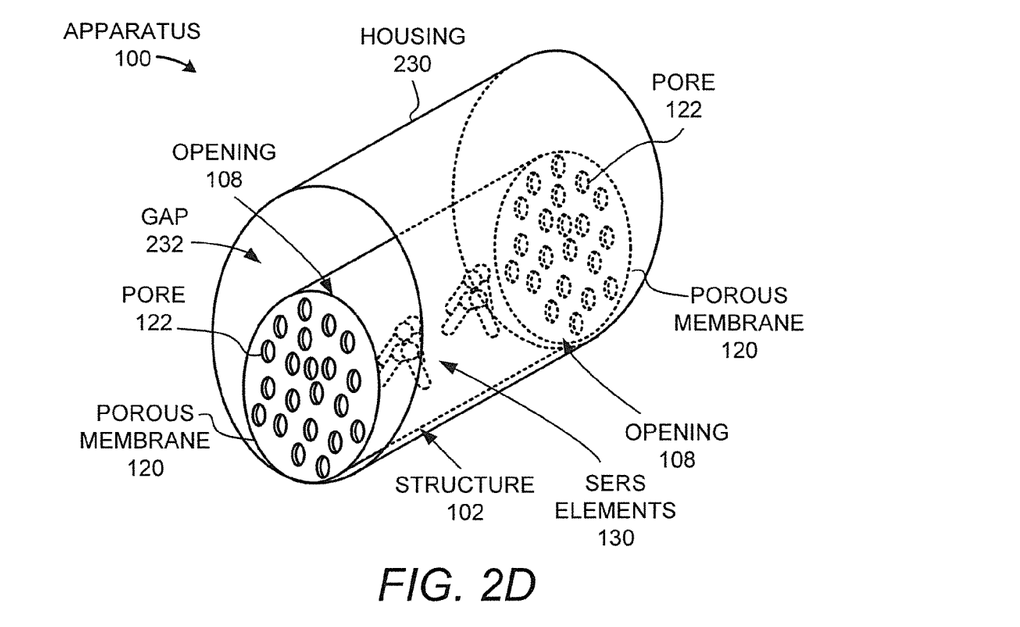
FIG. 2D shows an isometric view of an apparatus, according to another example of the present disclosure.

According to an example, a plurality of apparatuses 100 having porous membranes 120 that are covered by at least one removable membrane 210 may be arranged in an array 220, for instance, as shown in FIG. 2C. As shown in FIG. 2C, the array 220 includes a plurality of apparatus 100, each including a respective removable membrane 210. Alternatively, the plurality of apparatuses 100 may comprise a single apparatus 100 having a plurality of interior walls. One of the removable membranes 210 has been depicted as being removed to expose a porous membrane 120. In this regard, the removable membranes 210 may selectively be removed through application of a sufficiently intense light beam onto the removable membranes 210 or portions thereof to introduce fluid into respective ones of the apparatuses 100, for instance, to enable analysis to be performed on a fluid at different times. In another example, the removable membranes 210 may be fabricated of biodegradable materials that enable the removable membranes 210 to degrade at different times, e.g., seconds, minutes, hours, days, etc., thus exposing different ones of the apparatuses 100 to a surrounding fluid at different times. The array 220 of the apparatuses 100 therefore enables continuous monitoring of a fluid over a period of time, for instance, following implantation of the array 220 into a specimen.

Although each of the apparatuses 100 has been depicted as including a respective removable membrane 210, it should be understood that a single removable membrane 210 may instead be provided over all of the apparatuses 100. Additionally, a plurality of removable membranes 210 may be provided over respective sets of apparatuses 100. In these examples, a light beam may selectively be applied as desired over the apparatuses 100 to reveal the respective porous membranes 120 of the apparatuses 100.

With reference now to FIG. 2D, there is shown an isometric view of an apparatus 100, according to another example. In FIG. 2D, the structure 102 of the apparatus 100 is depicted as comprising a cylindrical shaped structure having openings 108 at opposite ends of the structure 102. In addition, SERS elements 130 are depicted as being positioned within the structure 102. Moreover, porous membranes 120 are depicted as covering each of the openings 108. In this example, the structure 102 comprises a mesh configuration and/or is formed of an optically transparent material to enable light to be emitted through the structure 102. In instances in which the structure 102 comprises a mesh structure, gaps in the mesh structure are sufficiently small to substantially prevent molecules having relatively large sizes from flowing into the structure 102. As such, the structure 102 may be formed to operate as a filter.

The apparatus 100 is also depicted as including a housing 230, within which the structure 102 is contained. As shown, the housing 230 has a relatively larger diameter than the structure 102, such that a gap 232 exists between the structure 102 and the housing 230. In one regard, as fluid flows through the housing 230, at least a portion of the fluid is able to flow through the housing 230 without substantially being impeded by the porous membrane 120. By way of particular example, the housing 230 comprises a stent sized to fit into an artery and blood is allowed to flow around the porous membrane 120 and the structure 102 through the gap 232.

The housing 230 may comprise any material suitable for implantation into a specimen, such as silicon, polymer, plastic, silver, titanium, etc. In addition, the housing 230 is formed to enable excitation light 312 emitted from an illumination source and Raman scattered light emitted to a detector to be transmitted therethrough. In this regard, the housing 230 is formed with a plurality of holes, for instance, as a mesh structure. In addition, or alternatively, the housing 230 is formed of an optically transparent material.

Figure 3:
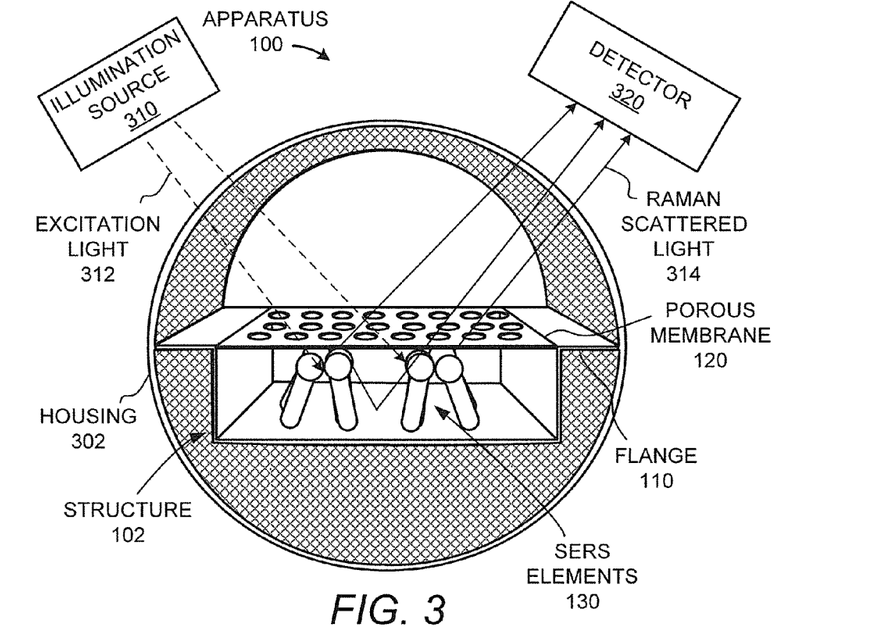
FIG. 3 shows a cross-sectional perspective view of a portion of an apparatus for performing spectroscopy, according to another example of the present disclosure.

Turning now to FIG. 3, there is shown a cross-sectional perspective view of a portion of an apparatus 100 for performing spectroscopy, according to another example. It should be understood that the apparatus 100 depicted in FIG. 3 may include additional components and that some of the components described—herein may be removed and/or modified without departing from a scope of the apparatus 100. It should also be understood that the components depicted in FIG. 3 are not drawn to scale and thus, the components may have different relative sizes with respect to each other than as shown therein.

As shown in FIG. 3, the apparatus 100 includes the structure 102, the porous membrane 120, and the SERS elements 130. The apparatus 100 is also depicted as including a housing 302, within which those components are contained. According to an example, the structure 102 and the flanges 110 are sized to fit within the housing 302, for instance, such that the flanges 110 contact the inner surface of the housing 302 and the structure 102 is held in a relatively stable position with respect to the housing 302 through frictional contact between the flanges 110 and the inner surface of the housing 302. In addition, or alternatively, an adhesive may be used to bond the flanges 110 to the housing 302. As a further alternative, the flanges 110 may be removed and the side walls 104 of the structure 102 may be frictionally or adhesively in contact with the inner surface of the housing.

The housing 302 may comprise any material suitable for implantation into a specimen, such as silicon, polymer, plastic, silver, titanium, etc. In addition, the housing 302 is formed to enable excitation light 312 emitted from an illumination source 310 and Raman scattered light 314 emitted to a detector 320 to be transmitted therethrough. In this regard, the housing 302 is formed with a plurality of holes, for instance, as a mesh structure. In addition, or alternatively, the housing 302 is formed of an optically transparent material.

According to an example, when the illumination source 310 emits an excitation light 312 (or equivalently, a pump light), such as a laser beam, an LED beam, etc., onto the Raman-enhancing elements 132, the Raman-enhancing elements 132 create near fields around the Raman-enhancing elements 132. The metallic nanoparticles (or other plasmonic structures) of the Raman-enhancing elements 132 also act to enhance the Raman emission process of the analyte molecules. The near fields around the Raman-enhancing elements 132 couple to analyte molecules (not shown) in the vicinities of the Raman-enhancing elements 132. As a result, Raman scattered light is emitted from the analyte molecules and the emission of the Raman scattered light 314 is enhanced by the Raman-enhancing elements 132. A portion of the Raman scattered light 314, which may be emitted in all directions from the analyte molecules near the Raman-enhancing elements 132, is emitted through the porous membrane 120, and in various examples, through the structure 102, which may then be collected by the detector 320, which may comprise a spectrometer, photodetectors, etc. The excitation light 312 and the Raman scattered light 314 also pass through the housing 302. In instances where the inner surfaces of the structure 102 are reflective, some of the Raman scattered light 314 may reflect off the inner surface and out through the porous membrane 120. The detector 320 is to generate electrical signals corresponding to the wavelengths of light contained in the detected Raman scattered light 314, which may be processed to determine Raman spectrum of the Raman scattered light 314 originating from the analyte molecules.

It should be understood that a relatively small section of the apparatus 100 has been depicted in FIG. 3. In this regard, a plurality of sets of structures 102, porous membranes 120, and SERS elements 130 may be provided within the housing 302 in a one or greater dimensional array. In addition, the housing 302 may comprise a relatively long structure, similar to various stent structures.

Figure 4A:
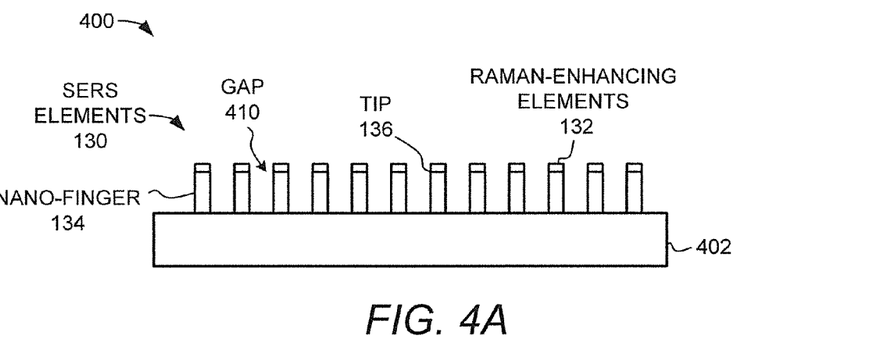
FIGS. 4A and 4B, respectively show side views of an array of the SERS elements depicted in FIGS. 1A-3 prior to and following collapse of the nano-fingers onto each other, according to an example of the present disclosure.
Figure 4B:
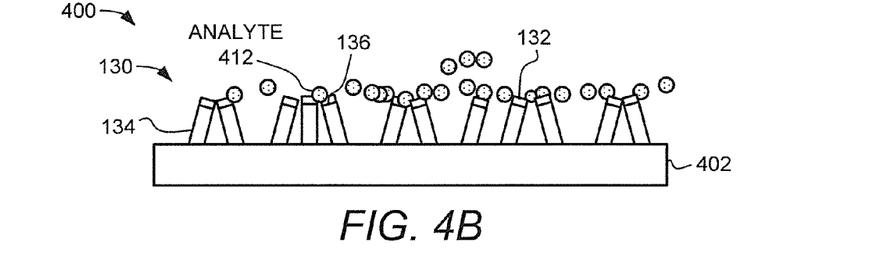

Turning now to FIGS. 4A and 4B, there are respectively shown side views of an array 400 of the SERS elements 130 depicted in FIGS. 1A-3 prior to and following collapse of the nano-fingers 134 onto each other, according to an example. As shown in FIGS. 4A and 4B, the array 400 includes a substrate 402 upon which the nano-fingers 134 extend. More particularly, the nano-fingers 134 are depicted as being attached to and extending above a surface of the substrate 402. The substrate 402 may be formed of any suitable material, such as, silicon, silicon nitride, glass, plastic, polymer, $SiO_2$, $Al_2O_3$, aluminum, etc., or a combination of these materials, etc. In addition, or alternatively, the substrate 402 may comprise the base 104 of the structure 102 or the array 400, including the substrate 402, may be positioned on the base 104.

According to an example, the nano-fingers 134 are formed of a relatively flexible material to enable the nano-fingers 134 to be laterally bendable or collapsible, for instance, to enable tips 136 of the nano-fingers 134 to move toward each other, as discussed in greater detail herein below. Examples of suitable materials for the nano-fingers 134 include polymer materials, such as, UV-curable or thermal curable imprinting resist, polyalkylacrylate, polysiloxane, polydimethylsiloxane (PDMS) elastomer, polyimide, polyethylene, polypropelene, polyurethane, fluoropolymer, etc., or any combination thereof, metallic materials, such as, gold, silver, aluminum, etc., semiconductor materials, etc., and combinations thereof.

The nano-fingers 134 are attached to the surface of the substrate 402 through any suitable attachment mechanism. For instance, the nano-fingers 134 are grown directly on the substrate 402 surface through use of various suitable nanostructure growing techniques. As another example, the nano-fingers 134 are integrally formed with the substrate 402. In this example, for instance, a portion of the material from which the substrate 402 is fabricated is etched or otherwise processed to form the nano-fingers 134. In a further example, a separate layer of material is adhered to the substrate 402 surface and the separate layer of material is etched or otherwise processed to form the nano-fingers 134. In various examples, the nano-fingers 134 are fabricated through a nanoimprinting or embossing process in which a template of relatively rigid pillars is employed in a multi-step imprinting process on a polymer matrix to form the nano-fingers 134. In these examples, a template may be formed through photolithography or other advanced lithography with the desired patterning to arrange the nano-fingers 134 in the predetermined arrangement. More particularly, for instance, the desired patterns may be designed on a mold, by E-beam lithography, photolithography, laser interference lithography, Focused Ion Beam (FIB), self-assembly of spheres, etc. In addition, the pattern may be transferred onto another substrate, for instance, silicon, glass, or polymer substrate (PDMS, polyimide, polycarbonate, etc.). Various other processes, such as, etching, and various techniques used in the fabrication of micro-electromechanical systems (MEMS) and nano-electromechanical systems (NEMS) may also be used to fabricate the nano-fingers 134.

A nano-finger 134 is defined, for instance, as an elongated, nanoscale structure having a length (or height) that exceeds by more than several times a nanoscale cross sectional dimension (for instance, width) taken in a plane perpendicular to the length (for instance, length>3×width). In general, the length is much greater than the width or cross sectional dimension to facilitate bending of the nano-finger 134 laterally toward one or more neighboring nano-fingers 134. In some examples, the length exceeds the cross sectional dimension (or width) by more than a factor of about 5 or 10. For example, the width may be about 100 nanometers (nm) and the height may be about 500 nm. In another example, the width at the bases of the nano-fingers 134 may range between about 10 nm and about 1 micrometer (μm) and the length may range between about 50 nm and 2 μm. In other examples, the nano-fingers 134 are sized based upon the types of materials used to form the nano-fingers 134. Thus, for instance, the more rigid the material(s) used to form the nano-fingers 134, the less the width of the nano-fingers 134 may be to enable the nano-fingers 134 to be laterally collapsible. In further examples, the nano-fingers 134 may form ridges in which two of three dimensions (for instance, length and height) exceed by more than several times a nanoscale cross sectional dimension (for instance, width).

The nano-fingers 134 have been depicted as having substantially cylindrical cross-sections. It should, however, be understood that the nano-fingers 134 may have other shaped cross-sections, such as, for instance, rectangular, square, triangular, etc. In addition, or alternatively, the nano-fingers 134 may be formed with one or more features, such as, notches, bulges, etc., to substantially cause the nano-fingers 134 to be inclined to collapse in particular directions. Thus, for instance, two or more adjacent nano-fingers 134 may include the one or more features to increase the likelihood that the nano-fingers 134 collapse toward each other.

The array 400 includes a substantially random distribution of nano-fingers 134 or a predetermined configuration of nano-fingers 134. In any regard, according to an example, the nano-fingers 134 are arranged with respect to each other such that the tips of at least two neighboring nano-fingers 134 are able to be brought into close proximity with each other when the nano-fingers 134 are in a collapsed state, for instance, less than about 10 nanometers apart from each other. By way of particular example, the neighboring nano-fingers 134 are positioned less than about 100 nanometers apart from each other. According to a particular example, the nano-fingers 134 are patterned on the substrate 402 such that neighboring ones of the nano-fingers 134 preferentially collapse into predefined geometries, for instance, triangles, squares, pentagons, etc.

The Raman-enhancing elements 132 comprise a plasmonic material such as, but not limited to, gold, silver, copper, platinum, aluminum, etc., or a combination of these metals in the form of alloys, or other suitable material that is able to support surface plasmons for field enhancement for Raman scattering. In addition, the Raman-enhancing elements 132 may be multilayer structures, for example, 10 to 100 nm silver layer with 1 to 50 nm gold over-coating, or vice versa. By definition herein, a plasmonic material is a material that supports plasmons.

Each of the tips 136 of the nano-fingers 134 has been depicted as including a respective Raman-enhancing element 132 disposed thereon. The Raman-enhancing elements 132, which may comprise metallic nanoparticles, may be deposited onto the tips 136 of the nano-fingers 134 through one of, for instance, physical vapor deposition (PVD), chemical vapor deposition (CVD), sputtering, etc., of metallic material, or self-assembly of pre-synthesized nano-particles.

As shown in FIG. 4A, the nano-fingers 134 are in a first position, in which the tips 136 are in a substantially spaced arrangement with respect to each other. The gaps 410 between the tips 136 may be of sufficiently large size to enable a liquid to be positioned in the gaps 410. In addition, the gaps 410 may be of sufficiently small size to enable the tips 136 of at least some of the nano-fingers 134 to be drawn toward each other as the liquid provided in the gaps 410 evaporates, through, for instance, capillary forces applied on the tips 136 as the liquid evaporates. FIG. 4B depicts the array 400 of nano-fingers 134 in a collapsed stated following evaporation of the liquid.

As shown in FIG. 4B, the tips 136 of some of the nano-fingers 134 have been drawn toward with each other. According to an example, the tips 136 of some of the nano-fingers 134 may be in and may remain in relatively close proximity to with each other for a period of time due to the capillary forces applied on adjacent ones of the nano-fingers 134 during and following evaporation of the liquid in the gaps 410 between the tips 136.

In any event, and in one regard, the tips 136 of the nano-fingers 134 are caused to be drawn toward each other to enhance Raman signal emission by analyte molecules 412 in the near fields of the Raman-enhancing elements 132 because the relatively small gaps between the Raman-enhancing elements 132 on the adjacent tips 136 create "hot spots" having relatively large electric field strengths.

According to an example, the nano-fingers 134 are positioned into the collapsed state depicted in FIG. 4B prior to the apparatus 100 being implanted.

Figure 5:
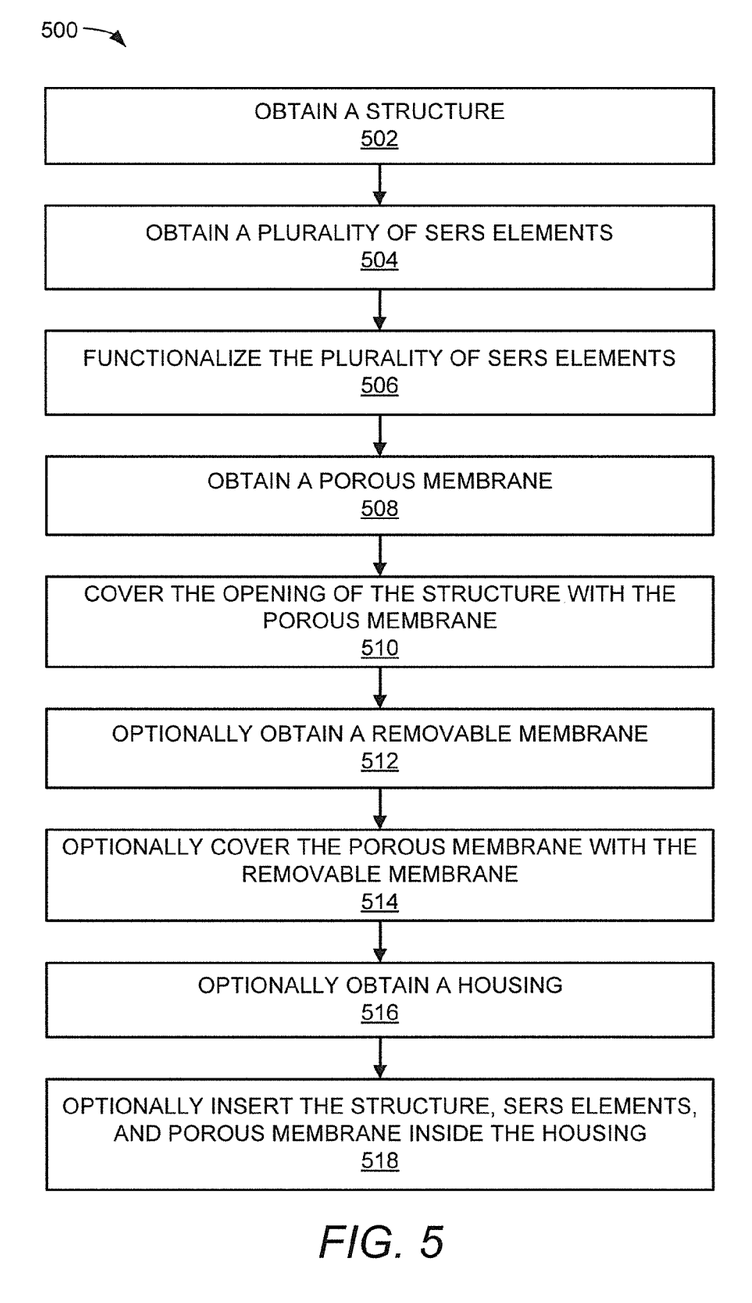
FIG. 5 shows a flow diagram of a method for fabricating an apparatus for performing spectroscopy, according to an example of the present disclosure.

Turning now to FIG. 5, there is shown a flow diagram of a method 500 for fabricating an apparatus for performing spectroscopy, according to an example. It should be understood that the method 500 depicted in FIG. 5 may include additional processes and that some of the processes described herein may be removed and/or modified without departing from a scope of the method 500. In addition, although particular reference is made herein to the apparatus 100 as being fabricated through implementation of the method 500, it should be understood that the method 500 may be implemented to fabricate a differently configured apparatus without departing from a scope of the method 500.

At block 502, a structure 102 is obtained. The structure 102 may be obtained through fabrication of the structure 102 in any of the manners discussed above. Alternatively, the structure 102 may comprise a pre-fabricated component and may thus be obtained from a manufacturer or supplier of the structure 102.

At block 504, a plurality of SERS elements 130 are obtained. The SERS elements 130 may be obtained through fabrication of the SERS elements 130 in any of the manners discussed above. Alternatively, the SERS elements 130 may be pre-fabricated on a substrate and may thus be obtained from a manufacturer or supplier of the SERS elements 130. According to a particular example, the SERS elements 130 comprise the Raman-enhancing elements 132 provided on the tips 136 of the nano-fingers 134, which may be fabricated in any of the manners discussed above. The obtaining of the SERS elements 130 also includes the positioning of the SERS elements 130 on the base 104 of the structure 102 either by direct fabrication on the base 104 or by fabrication of the SERS elements 130 on a substrate and positioning of the substrate onto the base 104.

At block 506, the SERS elements 130 may be functionalized to preferentially bind with a predetermined species as discussed above with respect to FIG. 1C.

At block 508, a porous membrane 120 is obtained. The porous membrane 120 may be obtained through fabrication of the porous membrane 120 in any of the manners discussed above. In addition, the porous membrane 120 may comprise any of the materials discussed above. Alternatively, the porous membrane 120 may comprise a prefabricated membrane and may thus be obtained from a manufacturer or supplier of the porous membrane 120.

At block 510, an opening 108 of the structure 102 is covered by the porous membrane 120. According to an example, the porous membrane 120 is adhered to the side walls 106 of the structure 102 to prevent fluid from being delivered into the structure 102 without being filtered by the porous membrane 120.

At block 512, a removable membrane 210 is optionally obtained. The removable membrane 210 may be obtained through fabrication of the removable membrane 210 in any of the manners discussed above. In addition, the removable membrane 210 may comprise any of the materials discussed above. Alternatively, the removable membrane 210 may comprise a prefabricated membrane and may thus be obtained from a manufacturer or supplier of the removable membrane 210.

At block 514 the porous membrane 120 is optionally covered by the removable membrane 210. According to an example, the removable membrane 210 is adhered to either or both of the side walls 106 of the structure 102 and the removable membrane 120 to prevent fluid from being delivered onto the porous membrane 120.

At block 516, a housing 302 that is sized and formed of a material to enable the housing 302 to be implanted into a specimen and for light to be emitted through the housing 302 is optionally obtained. The housing 302 may comprise any of the materials and sizes discussed above. In addition, the housing 302 may be obtained through fabrication of the housing 302. Alternatively, the housing 302 may comprise a prefabricated housing, such as a stent, and may thus be obtained from a manufacturer or supplier of the housing 302.

At block 518, at least the structure 102, the plurality of SERS elements 130, and the porous membrane 120, are optionally inserted into the housing in any of the manners discussed above.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. An apparatus for performing spectroscopy comprising:
   a structure having an opening;
   a plurality of surface-enhanced Raman spectroscopy (SERS) elements positioned within the structure; and
   a porous membrane covering the opening and the plurality of SERS elements, wherein the porous membrane is to allow a predetermined analyte to reach the SERS elements while substantially preventing other analytes from reaching the SERS elements, and wherein the porous membrane comprises functionalized receptors that bind to selected species in a fluid to thereby substantially prevent the selected species from entering into the opening of the structure.

2. The apparatus according to claim 1, wherein the porous membrane is formed of a material selected from a group consisting essentially of cellulose acetate, urethane based polymer, ethylene glycol based polymer, heparin-functionalized polymer, and a combination thereof.

3. The apparatus according to claim 1, wherein the porous membrane comprises a lipid bilayer supported on a porous sub-layer that covers the opening.

4. The apparatus according to claim 1, wherein the porous membrane comprises pores that are shaped that allow molecules having predetermined configurations to pass therethrough while preventing other molecules from passing therethrough.

5. The apparatus according to claim 1, wherein the structure comprises a plurality of openings and a plurality of porous membranes, and wherein each of the plurality of openings is covered by a respective porous membrane of the plurality of porous membranes.

6. The apparatus according to claim 1, wherein the plurality of SERS elements are functionalized to preferentially bind with a predetermined species.

7. The apparatus according to claim 1, further comprising:
   a housing sized and formed of a material to enable the housing to be implanted into a specimen and for light to be emitted through the housing, wherein the structure, the plurality of SERS elements, and the porous membrane are contained within the housing.

8. The apparatus according to claim 1, wherein the plurality of SERS elements comprises a plurality of a nano-fingers on which Raman-enhancing elements are attached to free ends of the nano-fingers, and wherein the Raman-enhancing elements on the free ends of at least two of the plurality of nano-fingers are in close proximity to each other.

9. The apparatus according to claim 1, further comprising:
   a removable membrane positioned over the porous membrane, wherein the removable membrane blocks the fluid from flowing through the porous membrane until the removable membrane is selectively removed.

10. An apparatus for performing spectroscopy, said apparatus comprising:
    a housing formed of a material and configuration to be implanted into a specimen while enabling light to be emitted through the housing;
    a structure having a base, side walls, and an opening, wherein the structure is contained within the housing;
    a plurality of surface-enhanced Raman spectroscopy (SERS) elements positioned within the structure; and
    a porous membrane covering the opening and the plurality of SERS elements, wherein the porous membrane is to allow a predetermined analyte to reach the SERS elements while substantially preventing other analytes from reaching the SERS elements, and wherein the porous membrane comprises functionalized receptors that bind to selected species in a fluid to thereby substantially prevent the selected species from entering into the opening of the structure.

11. A method for fabricating an apparatus for performing spectroscopy, the method comprising:
    obtaining a structure having an opening;
    obtaining a plurality of surface-enhanced Raman spectroscopy (SERS) elements, wherein the plurality of SERS elements are positioned on the base of the structure;
    obtaining a porous membrane; and
    covering the opening of the structure with the porous membrane, wherein the porous membrane is to allow a predetermined analyte to reach the SERS elements while substantially preventing other analytes from reaching the SERS elements, and wherein the porous membrane comprises functionalized receptors that bind to selected species in a fluid to thereby substantially prevent the selected species from entering into the opening of the structure.

12. The method according to claim 11, further comprising:
    functionalizing the plurality of SERS elements to preferentially bind with a predetermined species.

13. The method according to claim 11, further comprising:
    obtaining a removable membrane that is impervious to the flow of fluid; and
    covering the porous membrane with the removable membrane.

14. The method according to claim 11, further comprising:
    obtaining a housing sized and formed of a material to enable the housing to be implanted into a specimen and for light to be emitted through the housing; and
    inserting the structure, the plurality of SERS elements, and the porous membrane are inside the housing.

* * * * *